United States Patent
Leonhard et al.

(10) Patent No.: US 6,203,678 B1
(45) Date of Patent: Mar. 20, 2001

(54) SOLID ELECTROLYTE SENSOR FOR MEASURING GASEOUS ANHYDRIDES

(75) Inventors: Volker Leonhard, Kriftel; Ulrich Guth, Frankfurt am Main; Hartmut Erdmann, Steinbach/Taunus; Marianne Ilgenstein, Liederbach/Taunus; Heidrun Koppen, Kelkheim/Taunus; Dieter Fischer, Ludwigsburg, all of (DE)

(73) Assignee: Heraeus Electro-Nite International N.V., Houthalen (BE)

( * ) Notice: Subject to any disclaimer, the term of this patent is extended or adjusted under 35 U.S.C. 154(b) by 0 days.

(21) Appl. No.: 08/776,389
(22) PCT Filed: Jul. 28, 1994
(86) PCT No.: PCT/EP94/02506
§ 371 Date: Oct. 13, 1998
§ 102(e) Date: Oct. 13, 1998
(87) PCT Pub. No.: WO96/03642
PCT Pub. Date: Feb. 8, 1996

(51) Int. Cl.$^7$ .................................................. G01N 27/407
(52) U.S. Cl. .......................... 204/426; 204/424; 205/781; 205/784; 205/786.5
(58) Field of Search ...................................... 204/421–429

(56) References Cited

U.S. PATENT DOCUMENTS 4,976,991 * 12/1990 Ammende et al. ................... 204/424
5,178,744 * 1/1993 Nakazawa et al. ................... 204/426
5,194,134 * 3/1993 Futata et al. .......................... 204/426

FOREIGN PATENT DOCUMENTS

0182921 * 6/1986 (EP) .
0468249 A1 * 7/1991 (EP) .

OTHER PUBLICATIONS

Chu et al, "Thin and thick film electrochemical $CO_2$ sensors", *Solid State Ionics* vol. 53–56 (1992) Jul./Aug., pp. 80–84.*

* cited by examiner

Primary Examiner—T. Tung
(74) Attorney, Agent, or Firm—Antonelli, Terry, Stout & Kraus, LLP

(57) ABSTRACT

A galvanic solid electrolyte sensor for measuring gaseous anhydrides includes a ceramic solid electrolyte that has a material that conducts electrons, a measuring electrode that includes a pure or doped alkaline or alkaline earth salt and a reference electrode spatially separated from the measuring electrode and sealed off from the anhydride measuring gas by a gas-tight enclosure. The reference electrode is made of a metal material that conducts electrons. The gas-tight enclosure is made of a layer of a glass containing zirconium and lead that covers only the material of the reference electrode, with only a marginal area of this layer abutting the solid electrolyte.

3 Claims, 1 Drawing Sheet

HEATING ELEMENT

SOLID ELECTROLYTE SENSOR FOR MEASURING GASEOUS ANHYDRIDES

BACKGROUND OF THE INVENTION

The invention relates to a galvanic solid electrolyte sensor for measuring gaseous anhydrides, such as $CO_2$, SOx, and NOx and is based on a sensor like that disclosed in EP-0 182 921 B1.

For some time now, concentration of gaseous anhydrides has been determined using the Nernst equation in gas concentration cells with solid electrolytes, said electrolytes consisting of gas-tight, sintered pure doped alkaline or alkaline earth salts. Depending on the type of gas, solid electrolytes based on $Na_2CO_3$ are used for $CO_2$ sensors, those based on $NA_2SO_4$ for SOx sensors, and those based on $Ba(NO_3)_2$ for NOx. Such systems as is known permit measurements to be conducted with long-term stability if the solid electrolyte remains gas-tight. However, a reference gas with a constant oxygen and anhydride concentration is required, said gas being expensive to handle and produce industrially. There has been no lack of attempts to solve the problem of long-term gas tightness of the electrolyte and to produce a reference electrode that is easier to handle.

As is known, gas tightness can be improved for example by adding aliovalent cations to the alkaline salts which simultaneously increases conductivity (DD-PS 235 335 A1). Such systems however also generally have the disadvantage that the measuring and reference gas chambers must be separated from one another in a gas-tight manner, so that they cannot be manufactured economically, for example, by screen printing.

Nonetheless, systems with reference gas chambers are constantly under development, with EP-0 470 625 A2 proposing for example that a reference electrode layer made of Pt be applied to a heatable substrate and that a solid electrolyte, made of Nasicon for example, be placed on top of it, said electrolyte being covered on its upper surface by a measuring electrode, with a gas reference chamber being sealed off between the solid electrolyte and the substrate around the reference electrode layer by means of a glass covering that lies above the lateral surfaces of the substrate and the solid electrolyte, said electrolyte being completely enclosed as a result. Such an arrangement is once again not industrially effective, for example cannot be manufactured by the screen-printing process. It is also difficult to produce stable connections between the solid electrolyte material and the glass without reactions occurring between the two materials with time.

The problem of separating the measuring and reference gas chambers can be avoided by using a second solid electrolyte. Solid body cells have been proposed (German patent 40 22 136 C2) for measuring gaseous anhydrides such as $CO_2$ for example, said cells consisting of a combination of alkaline-ion-conducting solid electrolyte, formed from the anhydride, from $NA_2CO_3$ for example, and a ceramically stable usually dense material, Nasicon or $\beta$-$Al_2O_3$ for example, in which the same cation is mobile. Both solid electrolytes are provided with metal coatings with respect to which electrochemical equilibria can be created as a consequence of which an equilibrium cell potential or e.m.f. can be measured between the latter. In such arrangements, the electrochemical reaction must take place at the measuring electrode of the anhydride, for example, $CO_2$ and $O_2$, while only oxygen is effective on the reference side. The oxygen species that are then formed in the alkaline-ion-conducting ceramic solid electrolyte cannot migrate through the electrolyte so that interference with the electrode potential caused by the measuring current or gas exchange cannot be ruled out. Such problems make themselves felt in the form of long adjusting times and drift phenomena of the cell signal.

If a solid electrolyte that conducts oxide ions is used instead of one that conducts alkaline ions, a loadable oxygen reference electrode can be produced that forms the interface between this electrolyte and the one formed from the anhydride, but is gas-sensitive and must therefore be separated in a gas-tight manner from the measuring gas chamber, which in turn is not easy to accomplish.

All efforts to produce a reference electrode on solid electrolytes that conduct alkaline ions had in common the fact that an attempt was made to create conditions for the electrode reaction that were as reversible as possible. According to general understanding, such an electrode can only be one in which alkaline ion passage takes place through the phase boundary. Problems caused by current flow are compensated in that an alkaline ion current passes the phase boundary depending on the current direction and the required electrons come from the metal conductor, gold for example, or are given up to the latter.

The other possibility involves eliminating a metal/metal ion electrode (for example Na/Na+ electrode) by providing an $O_2$, metal/ceramic alkaline conductor electrode (called oxygen electrode for short). The disadvantage of such an oxygen electrode is that it can easily be disrupted even when sufficient oxygen enters because only a small amount of oxygen can react during the current flow and the conditions that block the electrode reaction become established very quickly. This electrode reaction can be disrupted by an electrochemical reaction with anhydrides that takes place in parallel when oxygen is present, so that mixed potentials can form as a result of the degree of interference.

The use of a metal/metal ion electrode for example sodium (1)/Na+ conducting solid electrolyte as the stable reference electrode like that proposed by J. Liu and W. Weppner in Solid State Comm. 76(1990), pages 311–313, is theoretically possible but neither safe nor easy to do (owing to the sodium which liquefies at measuring temperatures), so that such electrodes are not considered for mass application.

Improved stability of the reference electrode can be achieved by using systems which are both alkaline ion conducting and electron conducting. Alloys of noble metals and alkaline metals, for example sodium in gold, however are not very stable chemically at the measuring temperatures. In addition, the alkaline metal activity changes readily which in turn leads to a change in potential. Alkaline compounds of transition metal oxides, such as tungsten bronzes, in which the alkaline ion often occurs intercalated, usually have a greater phase width for alkaline ions and are also frequently poisonous. They must exhibit good adhesion and be applied to the solid electrolytes while protected from the measuring gas. The coating materials react with these systems in the long term, which can result in crack formation and thus the entry of measuring gas to the reference electrode and thus cause drift phenomena. The application of the reference and coating materials poses technical difficulties, said materials requiring adjustment to the solid electrolyte in terms of their coefficients of expansion so that such sensors are not simple to manufacture, for example, by screen printing.

It has also been proposed to coat the entire solid electrolyte not covered by the metal salt, said electrolyte having on opposite sides a reference electrode made of metal and a measuring electrode made of metal with the metal salt layer on top, with an electrically insulating cover layer made of ceramic, glass, or plastic (EP-0 182 921 B1). However, this still does not eliminate the disadvantages that result from the necessary combination of different materials. There is also the danger, as our own investigations have shown, that in the long term, the cover layer reacts with the solid electrolyte or, as a result of the impurities penetrating into the cover layer, the layer becomes more or less conductive at the operating temperature of the sensor and thus causes a diffusion potential and thus a drift in the sensor signal. Especially the glasses proposed for the cover layer can become electrically conducting through the inward diffusion of alkaline ions at the phase boundary. All in all, it was not possible in the tests that were conducted either to produce a stable boundary surface between the metal salt and the cover layer or a stable interface between the electrolyte and the cover layer.

Consideration was also given to using a metal/metal oxide mixture (for example Pd/PdO) with a thermodynamically defined constant oxygen partial pressure. The disadvantage of such electrodes is the temperature dependence of the oxygen partial pressure that becomes established. In addition, there are also the disadvantages associated with the gas-tight covering of such systems.

SUMMARY OF THE INVENTION

The goal of the invention is to provide a solid electrolyte sensor of the type according to the species which can be manufactured and remains stable in the long term by using electronically compatible techniques such as screen printing.

This was accomplished with the sensor of the present invention. In particular, the sensor is a Galvanic solid electrolyte sensor for measuring gaseous anhydrides. The sensor includes a ceramic solid electrolyte, that has a material that conducts electrons, a measuring electrode that includes a pure or doped alkaline or alkaline earth salt, and a reference electrode spatially separated from the measuring electrode and sealed off from the anhydride measuring gas by a gas-tight enclosure. The reference electrode is made of a metal material that conducts electrons, and the gas-tight enclosure comprises a layer of high melting point glass or glass that contains zirconium and lead, and covers only the material of the reference electrode that conducts electrons, with only a marginal area of this layer abutting the solid electrolyte. Sensors on this basis with low cross sensitivity to water vapor and atmospheric impurities or anhydrides that cannot be detected can be produced with which continuous measurement was possible and reference electrode was stable in the long term.

In the course of the attempts to produce such a sensor, the inventors made the accidental and completely surprising observation that contrary to the teaching in EP-0 182 921 B1 and the other known systems with or without reference gas chambers, it is not the entire solid electrolyte outside the metal salt that must be covered with glass for example, but instead stable sensors can be produced reproducibly when only the electron-conducting material of the reference electrode (preferably platinum, but also possibly inert semiconductor materials as well) is covered with glass so that only the marginal areas of this glass layer abut the solid electrolyte. In other words, only the area of the reference electron conductor that adjoins the ceramic solid electrolyte is covered with a gas-tight layer, thus producing a practically gas-tight seal for the electron-conducting reference electrode.

Since all the experts involved were unable to explain why this resulted in a stable functional system, a number of tests were conducted for example with different glasses and application techniques, such as screen printing followed by stoving, painting, or application of glass grains to be stoved. It turned out that when the sensor was printed on a substrate, reference electrodes that were always stable could be produced with different cover layer widths and margins, when a space, preferably in the range of several mm or more, was present between the measuring electrode and the covered reference electrode, in which space the solid electrolyte was not covered. In this case, interactions, diffusion potentials, and short circuit reactions could be reliably prevented between the boundary surfaces and/or electrodes.

Arrangements like that in EP-0 182 921 B1 with electrodes on the top and bottom of the solid electrolyte are also possible, with only the more or less thick marginal areas of the cover layer abutting the solid electrolytes, which layer otherwise remains uncovered up to the metal salt area. This arrangement however is not so advantageous as far as effective manufacture is concerned as the arrangement on a substrate.

In any event, the link between the reference electron conducting material such as Pt and Au and the cover layer, preferably glass, can be produced in an industrially simple and permanent fashion so that it adheres tightly and firmly. The relatively small interface between the cover layer and the solid electrolyte offers no technical problems.

One possible interpretation of the functional ability of the sensor according to the invention is the following. The material layer, preferably made of glass or a ceramic with a closed porosity with a maximally gas-sealing effect, which covers the reference electrode material that conducts electrons, contains both a certain small supply of air that is independent of the measuring temperature (but is not capable of being predetermined thermodynamically) and/or encloses the latter. Such air supplies for example can result from the roughness or porosity of the metal layer or its surface. In addition, this material layer protects the reference electrode from impurities that cause cross sensitivity and thus prevent the access of substances that could react in a parallel electrochemical fashion. Such impurities can include water vapor or sublimated alkaline salts ($Na_2CO_3$ for example) or reaction products of the latter with impurities ($Na_2SO_4$ for example) present in the air. The phenomena in the simplest case mean that a sensitivity to the anhydride to be detected develops also on the oxygen side of the ceramic alkaline ion conductor and thus increasingly, a gas-symmetric shell can be measured with a potential that runs opposite to the asymmetry potential. However, reaction products with water vapor or SOx appear on the surface of the ceramic alkaline ion conductor, resulting in a sensitivity to these gasses, making itself noticeable as the formation of a mixed potential and thus as deviations from the Nernst behavior that would be expected.

According to the invention, the reference electrode is limited to the (metal) layer conducting electrons. As a result, reactions with the solid electrolyte are prevented and short circuits and diffusion voltages that lead to drifting of the sensor signal in the long term, are avoided as well.

According to this theory, for example the glass that contains a small supply of air, present for example in the porous metal layer, or a ceramic with closed pores are considered as reference materials, with a chemical composition having only a slight influence on the stability of the reference signal. According to the classic theories of electrochemistry, such an electrode would be readily polarizable and therefore not to be used. The oxygen supply in such a material or enclosed thereby is clearly sufficient when the current flows, for example as a result of an inadvertent short circuit in the cell, to ensure a sufficiently large material reaction and after a certain start up time, to set a constant potential once again. It is not the supply of oxygen that is electrochemical limiting in this connection, but the course of the electrochemical reaction at the phase boundary between the alkaline-ion-conducting solid electrolyte/metal and the oxygen.

Regardless of whether this theory is true or not, the advantage is achieved over the demonstrated prior art that it is possible, without a defined larger and geometrically preferable reference gas volume, by direct technically simple application of the cover layer to the material of the reference electrode that conducts the electrons to create a stable sensor. No additional reference electrode layers are required.

To avoid reactions with the ceramic electrolyte, according to the invention, materials or ceramic compounds are also used according to the invention for the cover layers, such materials or compounds preferably containing the same alkaline ion as the ceramic solid electrolyte. These materials can be electrically conducting and contain Nasicon, $\beta$-$Al_2O_3$. and $Na_2ZrO_3$ for example.

Glasses containing zirconium and lead have been shown to be especially advantageous. It is generally true that glasses must have their thermal expansion behavior adapted to the substrate, for example, the (metal) layer that conducts the electrons, and the solid electrolyte, must be chemically compatible with both, must be able to provide a gas-tight covering, and should have a high transformation temperature of approximately 600° C. preferably.

According to the invention, the reference electrode can be produced by electronic-compatible techniques such as screen printing, foil casting, and subsequent sintering, as well as by surface coating techniques such as sputtering. This also applies to the gas-sensitive solid electrolyte materials of the measuring electrodes such as $Na_2CO_3$ made of a pure or doped alkaline or alkaline earth salt, formed from the anhydride to be measured as well as the solid electrolyte materials to be used that can be readily processed ceramically and are largely gas-tight, such as Nasicon and $\beta$-$Al_2O_3$, in which the same ion as in the alkaline or alkaline earth salt of the measuring electrode is mobile.

BRIEF DESCRIPTION OF THE DRAWING

In the following, the invention will be described with reference to the drawing. This shows in a schematic view an embodiment of the sensor according to the invention.

DETAILED DESCRIPTION OF THE PREFERRED EMBODIMENTS

Figure 1:
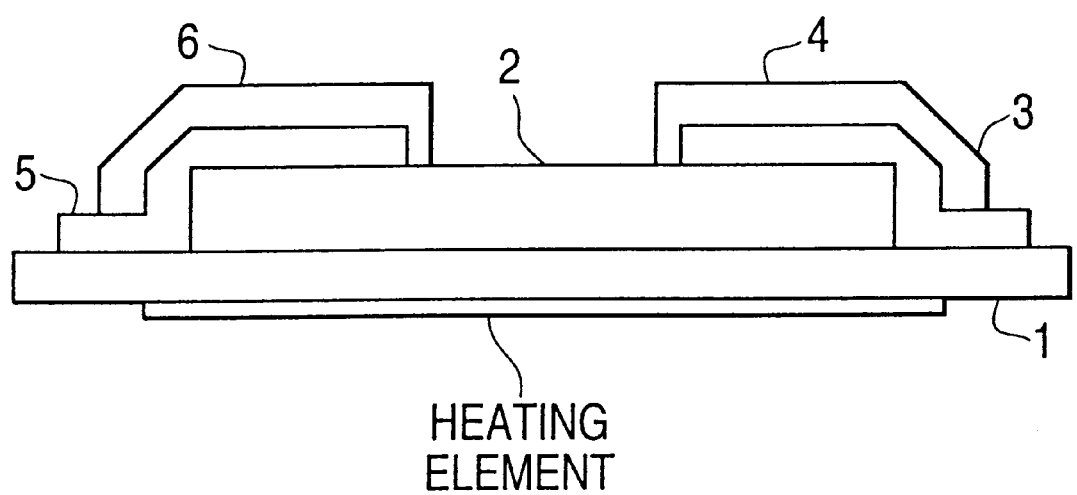

In FIG. 1, a ceramic solid electrolyte 2 is printed on a substrate 1 with (optionally integrated therein) heating element for reaching the operating temperature in known fashion. A metallic reference and a measuring electrode layer 3 and 5 respectively are printed on both sides and spaced apart from one another, said layers extending laterally over the planar electrolytes 2 to the substrate. The metal electrode layer 5 of the measuring electrode has a metal salt layer 6. Only one glass layer 4 is printed on top of reference metal electrode 3, with the inner marginal area of the layer abutting the solid electrolyte 2 as in the case of metal salt layer 6. In the embodiments, there are a few millimeters between the electrodes 3, 4 and 5, 6 in each case. In the schematic diagram, the marginal area of glass layer 4 is shown exactly at right angles. In practice, the transition is more or less uniform and abrupt. In addition, the thickness of the edge of the glass can be chosen arbitrarily so long as assurance is provided that a sufficient space still remains between the electrodes and the interactions between the interface which is always still comparatively small, between the glass and solid electrolyte 2 are negligible and do not lead to the abovementioned problems (interfering chemical interactions, separation of the layers, formation of mixed potentials).

In theory it is also possible to provide the electrodes on the front and back of solid electrolyte 2, whereby however the advantage of using efficient techniques such as screen printing technology is lost.

Conventional economical materials such as $Al_2O_3$ can be used as a substrate.

In the case of a $CO_2$ sensor, layers 3 and 5 consist of gold, 2 of Nasicon, and 6 of $Na_2CO_3$ or $BaCO_3$. The electrochemical cell has the following structure:

$$CO_2, O_2'Au\ Na_2CO_3, BaCO_3Na+\ conductor\ Au\ O_2''$$

In the case of an SOx sensor, layers 3 and 5 consist of Pt, 2 of $\beta$-$Al_2O_3$, and 6 of $(Na_2SO_4)_{0.9}(SrSO_4)_{0.1}$. The electrochemical cell has the following structure:

$$SOx, O_2'Pt(Na_2SO_4)_{0.9}(SrSO_4)_{0.1}Na+\ conductor\ PtO_2''$$

As the $CO_2$ sensitive solid electrolyte, in addition to $Na_2CO_3$ for example, $Li_2CO_3$ in the pure form or with addition of aliovalent ions and/or composite formers such as —$Al_2O_3$ can be used. As the ceramic stable solid electrolyte, in addition to compounds of Nasicon and Lisicon type, other complex, chemically-stable oxoanions may be used in which the same ion is moveable as in the anhydride-sensitive salt layer.

In the case of an NOx sensor that is made with the same construction as the above embodiment, layers 3 and 5 are made of platinum, 2 of $K_2YZr(PO_4)_3$ and 6 of $[Ba(NO_3)_2]_{0.9}[KNO_3]_{0.02}$. The electrochemical cell has the following structure:

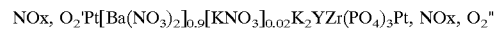

$$NOx, O_2'Pt[Ba(NO_3)_2]_{0.9}[KNO_3]_{0.02}K_2YZr(PO_4)_3Pt, NOx, O_2''$$

Very good results were obtained according to the invention using glasses containing zirconium and lead. In addition, other glasses, including inorganic compounds, ceramics with a closed porosity, or temperature stabile plastics are possible, for example —$Al_2O_3$, SiC, $Si_3N_4$, and plastics that are temperature-stable below 250° C. such as epoxy resins.

In the embodiment, glass layer 4 is applied so that it covers the part of metal layer 3 that is located directly above solid electrolyte 2. This should also be maintained in other sensor geometries. In the figure, a thin lateral rib of layer 4, that abuts solid electrolyte 2, serves to keep electron conductor 3 gas-tight even on its lateral area that faces measuring electrode 5, 6. On the other hand, the part of layer 3 that directly adjoins substrate 1 and does not count as a reference electrode in the electrochemical sense, can remain free for connections, as shown in FIG. 1. In other geometries it may be necessary to completely cover the entire metal layer on all edges. This is the case for example when a unilateral substrate is not provided and the reference electrode is applied for example only to the underside of the sensor. In this case, the electron-conducting layer of the reference electrode abuts the solid electrolyte material over its entire area and must therefore be covered completely.

What is claimed is:

1. Galvanic solid electrolyte sensor for measuring gaseous anhydrides, comprising a ceramic solid electrolyte, that has a material that conducts electrons, a measuring electrode that includes a pure or doped alkaline or alkaline earth salt, a reference electrode spatially separated from said measuring electrode and sealed off from the anhydride measuring gas by a gas-tight enclosure, said reference electrode being made of a metal material that conducts electrons, characterized in that the gas-tight enclosure comprises a layer of a glass containing zirconium and lead that covers only the material of the reference electrode that conducts electrons, with only a marginal area of this layer abutting the solid electrolyte.

2. Solid electrolyte sensor according to claim 1, characterized in that the gaseous anhydrides include $CO_2$, $SO_x$, and $NO_x$.

3. Solid electrolyte sensor according to claim 1, characterized in that the solid electrolyte is printed, together with the measuring electrode, the reference electrode and the material of the gas tight enclosure on a substrate.

* * * * *